(12) United States Patent
Kettunen et al.

(10) Patent No.: US 9,120,713 B2
(45) Date of Patent: Sep. 1, 2015

(54) SIMULTANEOUS PRODUCTION OF BASE OIL AND FUEL COMPONENTS FROM RENEWABLE FEEDSTOCK

(71) Applicant: Neste Oil Oyj, Espoo (FI)

(72) Inventors: Mika Kettunen, Helsinki (FI); Jukka Myllyoja, Vantaa (FI); Rami Piilola, Helsinki (FI); Goran Sandstrom, Helsinki (FI); Pekka Aalto, Porvoo (FI)

(73) Assignee: Neste Oil Oyj, Espoo (FI)

( * ) Notice: Subject to any disclaimer, the term of this patent is extended or adjusted under 35 U.S.C. 154(b) by 0 days.

(21) Appl. No.: 14/375,732

(22) PCT Filed: Nov. 1, 2012

(86) PCT No.: PCT/FI2012/051066
§ 371 (c)(1),
(2) Date: Jul. 30, 2014

(87) PCT Pub. No.: WO2013/113976
PCT Pub. Date: Aug. 8, 2013

(65) Prior Publication Data
US 2015/0018581 A1    Jan. 15, 2015

Related U.S. Application Data

(60) Provisional application No. 61/592,842, filed on Jan. 31, 2012.

(51) Int. Cl.
| | |
|---|---|
| *C07C 45/41* | (2006.01) |
| *C07C 1/22* | (2006.01) |
| *B01J 23/00* | (2006.01) |
| *C07C 1/24* | (2006.01) |
| *C11C 3/12* | (2006.01) |
| *C10L 1/04* | (2006.01) |
| *C10G 3/00* | (2006.01) |
| *B01J 23/883* | (2006.01) |
| *C11C 1/00* | (2006.01) |
| *C07C 45/54* | (2006.01) |
| *C10M 105/24* | (2006.01) |
| *B01D 3/00* | (2006.01) |
| *B01J 23/887* | (2006.01) |
| *C07C 5/27* | (2006.01) |
| *C10M 105/04* | (2006.01) |
| *C10M 177/00* | (2006.01) |
| *B01J 37/20* | (2006.01) |
| *B01J 35/00* | (2006.01) |
| *B01J 21/06* | (2006.01) |
| *B01J 23/04* | (2006.01) |

(52) U.S. Cl.
CPC . *C07C 1/24* (2013.01); *B01D 3/009* (2013.01); *B01J 23/883* (2013.01); *B01J 23/8872* (2013.01); *C07C 1/22* (2013.01); *C07C 5/2735* (2013.01); *C07C 5/2737* (2013.01); *C07C 45/41* (2013.01); *C07C 45/54* (2013.01); *C10G 3/42* (2013.01); *C10G 3/44* (2013.01); *C10G 3/45* (2013.01); *C10G 3/46* (2013.01); *C10L 1/04* (2013.01); *C10M 105/04* (2013.01); *C10M 105/24* (2013.01); *C10M 177/00* (2013.01); *C11C 1/005* (2013.01); *C11C 3/123* (2013.01); *B01J 21/063* (2013.01); *B01J 23/04* (2013.01); *B01J 35/0006* (2013.01); *B01J 37/20* (2013.01); *C07C 2523/16* (2013.01); *C07C 2523/42* (2013.01); *C07C 2523/44* (2013.01); *C07C 2523/46* (2013.01); *C07C 2523/745* (2013.01); *C07C 2523/75* (2013.01); *C07C 2523/755* (2013.01); *C10L 2200/0484* (2013.01)

(58) Field of Classification Search
CPC ........ C07C 45/41; C07C 1/22; C07C 5/2735; C07C 5/2737; C10M 177/00; B01J 23/8872
USPC ............ 568/397; 585/310; 502/310; 422/187
See application file for complete search history.

(56) References Cited

U.S. PATENT DOCUMENTS

| | | | | |
|---|---|---|---|---|
| 8,048,290 | B2 * | 11/2011 | Knuuttila et al. ............... | 208/64 |
| 2007/0161832 | A1 | 7/2007 | Myllyoja et al. | |
| 2009/0247799 | A1 * | 10/2009 | Myllyoja et al. .............. | 585/240 |

FOREIGN PATENT DOCUMENTS

WO    2007068799 A2    6/2007

OTHER PUBLICATIONS

International Search Report for PCT/FI2012/051066 dated Feb. 5, 2013.
James et al: "A review on conversion of triglycerides to on-specification diesel fuels without additional inputs", International Journal of Energy Research, May 2012, 36-6, 691-702.
Database Compendex [Online] Engineering Information, Inc. for James et al: "A review on conversion of triglycerides to on-specification diesel fuels without additional inputs", May 2012.
Nagashima et al: "Ketonization of carboxylic acids over CeO2-based composite oxides", Journal of Molecular Catalysis, Mar. 2005, 227-1,2, 231-239.

* cited by examiner

*Primary Examiner* — Sikarl Witherspoon
(74) *Attorney, Agent, or Firm* — Andrus Intellectual Property Law, LLP

(57) ABSTRACT

The present invention provides a method for simultaneous production of components suitable for production of base oil and fuel components. In the method a feedstock comprising fatty acids and/or fatty acid esters is entered into a reaction zone and subjected to a ketonization reaction in the presence of a dual catalyst system. This system is configured to perform a ketonization reaction and a hydrotreatment reaction, under hydrogen pressure. Subsequently ketones are obtained.

12 Claims, No Drawings

SIMULTANEOUS PRODUCTION OF BASE OIL AND FUEL COMPONENTS FROM RENEWABLE FEEDSTOCK

CROSS REFERENCE TO RELATED APPLICATION

The present application is the U.S. national stage of International Application PCT/FI2012/051066, filed Nov. 1, 2012, which international application was published on Aug. 8, 2013, as International Publication No. WO2013/113976. The International Application claims priority to U.S. Provisional Patent Application No. 61/592,842, filed Jan. 31, 2012, the contents of which are incorporated herein by reference in their entireties.

FIELD OF THE INVENTION

The present invention relates to the manufacture of hydrocarbons useful as fuels and lubricants from renewable feedstock such as biological oils and fats. In particular, the present invention relates to efficiently extending the carbon chain length of hydrocarbons from renewable feedstock via catalytic reactions.

BACKGROUND

The use of recycled oils and renewable raw materials in the production of transportation fuels and base oils for lubricants is an object of interest. The use of renewable raw materials of biological origin instead of non-renewable fossil raw materials for production of hydrocarbon components can be desirable. The fossil raw materials are exhaustible and they have harmful effects on atmosphere and environment.

Biological oils have previously been transesterified to form biodiesel (fatty acid methyl esters; FAME) and biolubricant components (lube esters). The use of lube esters is limited to a few special applications such as oils for refrigerator compressor lubricants, bio-hydraulic oils and metal working oils. Lube esters are used mainly in additive scale in regular automotive and industrial lubricants, because of the technical problems associated with them. Lube esters are polar compounds and suffer from greater seal-swelling tendency than pure hydrocarbons. In addition, lube ester oils are hydrolysed more easily to acids, which in turn cause corrosion on lubricating systems. Lubrication oils consisting of pure hydrocarbon structures are therefore favoured, since they do not suffer from these problems. It is therefore desirable to find ways of producing hydrocarbon containing lube oil components also from renewable sources.

Lube range components (C24-C43) can be produced from free fatty acids in a method where two free fatty acid molecules react with each other forming a ketone. The carbon number of the formed ketone back-bone is the sum of the carbon atoms in the two fatty acids minus one carbon, due to the release of one molecule of $CO_2$ during the ketonisation reaction. The catalysts used in these reactions are typically metal oxides.

Metal oxide ketonisation catalysts suffer from several drawbacks. The catalysts cannot withstand the presence of double bonds or triglycerides during the ketonisation reaction, which both are typically present in biological oils. Therefore, compounds with double bonds must be saturated and triglycerides are generally removed prior to leading the feedstock into the ketonisation unit. This is typically performed by distilling the free fatty acids and employing a pre-hydrogenation unit before the actual ketonisation unit. Furthermore, if noble metal catalysts are used in the double bond hydrogenation, sulphur and nitrogen traces will shorten the catalyst life significantly by deactivation and passivation of the metal sites of the catalyst. The ketonisation units therefore can require a very cumbersome pre-treatment of the triglyceridic biological oils.

In addition, ketonisation reaction of fatty acids is typically done using gas phase introduction of free fatty acids. Due to the low vapour pressure of fatty acids, vaporisation of fatty acids needs much carrier gas, which requires a large unit.

Ketones can be hydrodeoxygenated to paraffins using a hydrotreatment catalyst at 200-350° C. and hydrogen pressure of 1-5 MPa. The n-paraffins formed by hydrodeoxygenation of ketones can be hydroisomerised and produce branched iso-paraffins (typically methyl-paraffins).

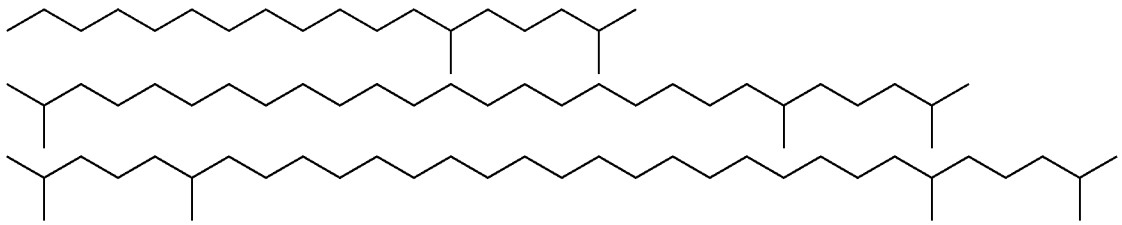

i-C35

Formation of hydrocarbon base oil components by ketonisation of free fatty acids, using a metal oxide catalyst in gas phase is demonstrated in the publication WO2007068795, the metal in the metal oxide catalyst being preferably Na, Mg, K, Ca, Sc, Cr, Mn, Fe, Co, Ni, Cu, Zn, Sr, Y, Zr, Mo, Rh, Cd, Sn, La, Pb, Bi, or a rare earth metal on a laterite, bauxite, titanium dioxide, silica and/or aluminium oxide support. The formed ketones were subsequently hydrodeoxygenated and isomerized to paraffinic lube oil components. Publication EP 591297 describes a method for producing a ketone from fatty acids by pyrolysis reaction using a magnesium oxide catalyst. EP 0457665 discloses a method for producing ketones from triglycerides, fatty acids, fatty acid esters, fatty acid salts, and fatty acid anhydrides using a bauxite catalyst containing iron oxide. All these methods suffer from the above described disadvantages.

Production of a hydrocarbon mixture comprising fuel components and base oil components would be economically advantageously carried out utilising the same process unit or equipment. Base oil components are possible to retrieve as side products to some extent. However, the practical production process is challenging due to different requirements for reactions and reaction conditions.

Publication US2011107656 describes a method for processing triglyceride-containing, biologically-derived oils to provide for base oils and diesel fuels, wherein a partial oligomerization of unsaturated fatty acids contained therein yields a mixture from which the base oils and diesel fuels are extracted. Dimerization, trimerization or oligomerization of unsaturated fatty acids and following hydrodeoxygenation, forms highly branched and cyclic hydrocarbon components and even aromatic compounds. Viscosity index of these mixtures is rather high, typically greater than 120.

To overcome the above described deficiencies, there is an obvious need for a method to produce efficiently and simultaneously nonpolar, saturated and linear base oil components and fuel components complying with the quality requirements for high-quality base oils, from renewable sources.

SUMMARY OF THE INVENTION

The object of the present invention is to provide a method capable of simultaneously producing components suitable for producing both base oil components and fuel components from renewable feedstock.

A further object of the present invention is to provide a method to produce nonpolar saturated base oil components and fuel components complying with the quality requirements for high-quality base oils and fuel components.

A further object of the present invention is to provide a method suitable for producing simultaneously base oil components and fuel components from renewable feedstock wherein the performance and life time of the used catalyst can be extended, and advantageously the economics of the process enhanced.

A yet further object of the present invention is to provide a method for producing base oil components and fuel components complying with the quality requirements for high-quality base oils wherein the feedstock used may comprise a large variety of starting materials, such as free fatty acids, typically decreasing the process efficiency, especially decreasing the catalyst life cycle.

It was surprisingly found that a catalyst system comprising a first catalyst capable of performing a ketonisation reaction and a second catalyst capable of performing a hydrotreatment reaction i.e. a dual catalyst system, can be utilized to efficiently carry out the production of linear base oil range ketones and fuel range paraffins without operational problems. The production into base oil components and fuel components, even in high concentration, can be performed from a feedstock containing traditionally problematic renewable starting materials such as free fatty acids and/or triglycerides. The mixture of base oil range paraffins is formed according to the method of the present invention by a ketonisation reaction of fatty acids or fatty acid esters under hydrogen partial pressure, resulting in a C(2n−1)-ketone from two C(n)-fatty acids.

The formed ketones may be processed further by hydrodeoxygenation to form n-paraffins in a final hydrodeoxygenation step. The n-paraffins may further be isomerized to produce high quality base oil components and fuel components from the renewable feedstock.

In the first aspect, the present invention provides a method for ketonisation under hydrotreatment conditions to produce suitable components for base oil production and fuel components as depicted by claim 1.

In the second aspect, the present invention provides a further method for producing base oil components of the carbon range C24-C43 and fuel components of the carbon range C5-C23 as depicted by claim 8.

The third aspect of the present invention provides a dual catalyst system depicted by claim 9. The dual catalyst system is suitable for use in a combined ketonisation and hydrotreatment reaction as depicted by claim 1 and 8.

A further aspect is a production system for simultaneous production of base oil and fuel components (a) at least one reaction unit comprising at least one reaction rone including a dual catalyst system configured to perform a keionisation reaction and a hydrotreatment reaction under hydrogen pressure for producing ketones and linear hydrocarbons, and (b) at least one reaction unit comprising at least one reaction zone configured to perform hydrodeoxygenation to said ketones into linear hydrocarbons, and (c) at least one reaction unit comprising at least one reaction zone configured to isomerize said linear hydrocarbons; and (d) at least one distillation installation configured to separate base oil components from fuel components; wherein at least one reaction unit (a) is connected to at least one reaction unit (b), and wherein at least one reaction unit (b) is connected to at least one distillation installation (c), and wherein at least one reaction unit (c) is connected to at least one distillation installation (d), wherein the system further comprises a flow path for recycling hydrocarbons from unit (b), (c) or (d) back to unit (a).

The advantages of the methods of the present invention are that the dual catalyst system is able to function efficiently and withstand conditions typically considered challenging for a ketonisation catalyst alone. The use of this dual catalyst system enables the presence of double bond containing components or triglyceridic components in the feedstock. Catalytic deactivation can be suppressed. The feedstock may also comprise free fatty acid, in particular in a high concentration. Moreover, surprisingly liquid hydrocarbon components can be used as a feed without the need of high energy consuming vaporisation of fatty acid feed prior to feed introduction to reactor. Traditionally ketonisation catalysts have required introduction of the feed in gaseous phase. Vaporization of fatty acids requires high energy consumption due to their low vapour pressure.

A yet further advantage is that the cumbersome pre-treatment of a typical feedstock, i.e. saturation of double bonds and separation of free fatty acids from triglycerides, can be avoided.

The method of the present invention is able to provide simultaneously both base oil components and fuel components, and moreover, these produced components show excellent technical quality fulfilling the most advanced standardised specifications.

DETAILED DESCRIPTION OF THE INVENTION

Definitions

By "ketonisation" is meant a ketonisation reaction i.e. the formation of a ketone through a chemical reaction of two compounds, producing molecule which is bigger than original reacting molecules. The ketone can be formed from two oxo-compound such as ester, aldehyde, carboxylic acid or other suitable oxygen containing starting material, particularly fatty acids, corresponding esters, aldehydes, anhydrides, and metal salts. In the reaction the functional groups of the feedstock react with each other yielding ketones. The ketonisation reaction of two carboxylic acids proceeds through a reaction intermediate to give a ketone, water and carbon dioxide liberating in the reaction. The ketonisation reaction of fatty acids or fatty acid esters result in a C(2n−1)-ketone from two C(n)-fatty acids. The two fatty acids can also be of different chain lengths. The ketonisation reaction differs from e.g. typically used oligomerisation reactions, in that a linear carbon backbone is formed instead of a highly branched hydrocarbon.

Here "lubricant" means oil which consists of base oil components and additives.

Here "base oil" means oil molecules which can be used as lubricant components. The carbon number range of base oil is from about C24-C43.

Here "fuel oil" means oil molecules which can be used as fuel oil components in automotive engines. The carbon number range of fuel oil is C23 or lower.

Viscosity index is a measure of base oil which tells how much the viscosity of base oil changes with temperature. The higher value means better base oil which can maintain its viscosity better at a broader temperature range. Good quality base oil has low enough viscosity for running at cold temperature and is still viscous enough at high temperature.

Here by "hydrotreatment" is meant a catalytic process which removes oxygen from organic oxygen compounds (hydrodeoxygenation, HDO), sulfur from organic sulfur compounds (hydrodesulfurisation, HDS), nitrogen from organic nitrogen compounds (hydrodenitrogenation, HDN) and halogens, for example chlorine from organic chloride compounds (dehydrochlorination, HDCl) typically, as well as saturation of carbon-carbon double bonds under a hydrogen pressure.

Here by "partial hydrotreatment" is meant a hydrotreatment reaction which removes oxygen, sulphur, nitrogen or halogens only partially, part of the organic compounds will remain.

Here "deoxygenation" is understood to mean the removal of oxygen from organic molecules, such as fatty acid derivatives, alcohols, ketones, aldehydes or ethers by any means previously described.

Here "hydrodeoxygenation" (HDO) of triglycerides or other fatty acid derivatives is understood to mean the removal of oxygen as water by the means of molecular hydrogen under the influence of a catalyst.

Here "decarboxylation/decarbonylation" of triglycerides or other fatty acid derivatives is understood to mean removal of oxygen as $CO_2$ (decarboxylation) or as CO (decarbonylation) with or without the influence of molecular hydrogen. Decarboxylation and/or decarbonylation reactions are together referred to as decarb-reactions.

Here "hydrocracking" is understood as catalytic decomposition of organic hydrocarbon materials under hydrogen pressure.

Here "hydrogenation" means saturation of carbon-carbon double bonds by means of molecular hydrogen under the influence of a catalyst.

Here "isoparaffins" mean alkanes having one or more side chains, typically mono-, di-, tri- or tetramethylalkanes.

Here purification of feedstock is understood as removal of impurities such as metals and phosphorus.

Feedstock

Typical basic structural unit of plant and fish oils and animal fats is triglyceride. Triglyceride is an ester of glycerol with three fatty acid molecules having the general structure of formula 1 below:

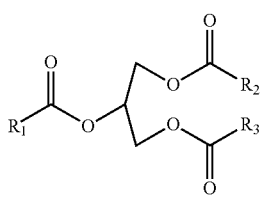

(1)

wherein $R_1$, $R_2$ and $R_3$ represent C4-C26 hydrocarbon chains. The length of the hydrocarbon chain is typically 18 carbons (C18). C18 fatty acids are typically bonded to the middle hydroxyl group of glycerol. Typical carbon numbers of the fatty acids linked to the two other hydroxyl groups are even, are generally between carbon numbers C14 and C22. Free fatty acids may be produced industrially by fat splitting or hydrolysis of triglycerides, with the removal of glycerol. Vegetable oils also comprise free fatty acids.

The feedstock of the present invention comprises fatty acids and/or fatty acid esters, originating from renewable sources such as plant oils, fish oils and animal fats. Preferably, the fatty acid esters comprise triglycerides, such as those of formula 1.

The method of the present invention is well suited for a feedstock containing a high extent of free fatty acids. The amount of free fatty acids may be up to 100%. Typically, commercially available feedstock comprises free fatty acids and/or triglycerides. The method of the present invention is capable of utilising these commercially available feedstocks with good yield and without deactivation of the used catalysts.

For example, triglycerides of palm oil comprises about 45% by weight of saturated fatty acids, about 42% by weight of monounsaturated fatty acids and about 8% by weight of polyunsaturated fatty acids. In one embodiment the feedstock of the present invention comprises palm oil or palm oil fatty acid, in another embodiment the feedstock is a mixture of palm oil fatty acid from 20 to 40% by weight and palm oil from 60 to 80% by weight. In yet another embodiment the feedstock of the present invention comprises palm oil and stearic acid, i.e. a mixture of stearic acid from 20 to 40% by weight and palm oil from 60 to 80% by weight.

Decomposition of triglycerides and fatty acid derivatives forms more free fatty acids, or other oxygenates which can further undergo ketonisation reaction and produce more base oil range molecules. Partial hydrotreatment of triglycerides facilitates controlled decomposition of the triglyceride molecules contrary to the uncontrolled thermal cracking. Thermal cracking is mainly unselective decomposition, whereas heat treatment reactions such as hydrodecomposition provides more selectivity.

During the combined ketonisation and hydrotreatment reaction double bonds are hydrogenated first, prior to ketonisation/hydrodeoxygenation, and therefore, minimize the double bond reactions such as oligomerisation, which creates poorer base oil and lubricant components with lower viscosity index.

The feedstock may be purified before entering it into the processing unit. Decrease of the metal and phosphorus content of the feedstock is preferred using the commonly known and available purification methods, including but not limited to bleaching, deodorization and degumming.

Pre-treatments, such as saturation of unsaturated components or reacting or removing triglycerides from biological oils, are not necessary in the method of the present invention.

In addition, the feedstock is preferably at least partly, more preferably completely, in liquid form when entered into the ketonisation step i.e. to the reaction zone wherein ketonisation takes place. Thus, separate vaporisation of the fatty acids is not necessary and the use of large amounts of carrier gas can be avoided.

Combined Ketonisation and Hydrotreatment Step

According to the first aspect of the present invention the feedstock comprising fatty acids and/or fatty acid esters, and optionally product recycle, is introduced into a reaction zone. Ketones are formed therein through a ketonisation reaction from said fatty acids and/or fatty acid esters, or their reaction products or derivatives. The feedstock is entered into the reaction zone and subjected to ketonisation under hydrogen pressure. The ketonisation reaction is carried out using a dual catalyst system configured to perform ketonisation reactions and hydrotreatment reactions.

In the present invention a ketonisation reaction takes place under hydrotreating conditions wherein the feedstock is at least partly ketonised and triglycerides, fatty acids and fatty acid derivatives are at least partly hydrotreated, such as deoxygenated, denitrogenated and/or desulphurisated. The degree of ketonisation is typically over 5%, preferably from 5-25%. When maximising base oil production ketonisation degree can be up to 90%. During the ketonisation and partial hydrotreatment, such as hydrodeoxygenation, of fatty acids $H_2O$, $CO_2$, CO, $H_2S$ and $NH_3$ gases are released and removed from the oil products. If the feed comprises triglycerides also propane is formed from the glycerol backbone. The simultaneous, or mixed, ketonisation and hydrotreating reactions are performed in the presence of the dual catalyst system and under hydrogen pressure.

The method according to the present invention for simultaneous production of components suitable for production of base oil and fuel components, therefore comprises the steps of:
a) introducing a feedstock comprising fatty acids and/or fatty acid esters into a reaction zone, and
b) subjecting said feedstock to a ketonisation reaction in said reaction zone in the presence of a dual catalyst system configured to perform a ketonisation reaction and a hydrotreatment reaction, under hydrogen pressure, and
c) obtaining from said ketonisation reaction ketones in addition to linear hydrocarbons from said fatty acids and/or fatty acid esters.

Under these conditions the increase of hydrocarbon chain length is possible through a ketonisation reaction without deactivation of the catalyst system. The advantages in using a ketonisation reaction together with a hydrotreatment reaction are directed to reactions taking place at desired locations of the carbon chain instead of any unsaturated position as is the case with e.g. oligomerisation. Fast hydrogenation of double bonds prevents side reactions like oligomerisation or coking of the catalyst system. Hydrogenation activity also prevents the formation of compounds heavier than double the size of original fatty acid. This phenomenon gives proper viscosity of base oil for high performance engine applications (4-6 cSt). Formation of higher molecular compounds increases the absolute viscosity of base oil (7-8 cSt).

Formation of base oil range components through ketonisation is also advantageous compared to oligomerisation since the molecular weight distribution of the base oil components is narrow. Biological material typically predominately contains C16 and C18 fatty acids, from which C31, C33 and C35 ketones are formed. Shorter fatty acids can also be used and resulting in base oil components with lower kinematic viscosity (KV). Shorter fatty acids are also typically highly saturated and cannot thus be oligomerised.

In the reaction zone the triglycerides of the feedstock are preferably partially hydrotreated, such as hydrodeoxygenated, and partially decomposed to intermediate components like free fatty acids which are able to further undergo a ketonisation reaction and subsequent hydrotreatment, such as hydrodeoxygenation. In a preferred embodiment the feedstock to be treated further comprises fatty acids which are already partly ketonised and triglycerides, fatty acids and fatty acid derivatives which are already partly deoxygenated, denitrogenated or desulphurisated. Free fatty acids may be formed during decomposition reactions of fatty acid esters or triglycerides providing excess of base oil components. These reactions are called pyrolytic elimination of esters, which form fatty acids. Performing hydrotreatment reactions partially enables ketonisation reactions of fatty acids and the handling of reaction heat caused by hydrotreatment without enormous product recycling, which is typical for highly exothermic reactions. High dilution of feed reduces the bimolecular reactions like ketonisation.

Products from the reaction zone, preferably the obtained ketones, are preferably introduced to a further final hydrodeoxygenation step for removal of any oxygen traces. The product of the final hydrodeoxygenation step is n-paraffins in diesel range (C11-C23) and in the base oil range (C24-C43). The formed n-paraffins are preferably converted into fuel and base oil range branched alkanes using isomerization, with a high base oil yield of good quality and fuel components with low cold flow properties.

The present invention discloses the combination of the bio base oil formation and fuel component formation by ketonisation of free fatty acids with the hydrotreatment of triglyceridic feedstock to fuel components over a dual catalyst system. The dual catalyst system can hydrogenate double bonds and remove oxygen from oxygenate components simultaneously with providing a ketonisation reaction. Therefore, separate double bond saturation unit is not needed for these purposes. The method according to this invention can also operate with triglycerides and unexpected high concentrations of free fatty acids. The co-production of long chain ketones and fuel components suitable in diesel and kerosene applications, which are bio based, calls for the control and optimization of the reaction conditions, due to the two simultaneous opposite reaction routes. The ketonisation and hydrotreatment reactions are competing reactions but also have complementing features like simultaneous hydrodeoxygenation of ketones produced and providing protection for the catalyst materials used. Hydrotreatment reaction inhibits also overaldol condensation. Moreover, free fatty acids are formed at partial hydration conditions suitable for further processing into base oil components.

Preferably, pressure and temperature in said reaction zone under the combined ketonisation and hydrotreatment reactions are selected in a way to maintain at least part of said feed composition in liquid phase. As mainly partial reactions are desired mild reaction conditions are favoured. There is no need to evaporate the feed thus enabling a decrease in reactor volume.

The combined ketonisation and hydrotreatment step is done at hydrogen pressure. Preferably the hydrogen pressure (overpressure) in the reaction zone is less than 10 MPa, more preferably from 0.1 to 5 MPa, i.e. from 1 to 3 MPa.

The combined ketonisation and hydrotreatment reaction temperature range in the reaction zone is preferably from 200 to 450° C., more preferably from 280 to 450° C., and most preferably from 310 to 400° C. The reaction rate is increased at higher temperature, but it favours cracking and other side reactions like aromatisation and coking.

The amount of hydrogen used is defined by the ratio of hydrogen ($H_2$) feed to feedstock, preferably liquid feed (i.e. triglycerides, free fatty acids). A low hydrotreatment activity is favoured as only partial hydrotreatment is desired.

In one embodiment this ratio is from 100 to 600 NI/l, more preferably from 100 to 500 NI/l. The sulfur content in the feed may be from 0 w-ppm to 10000 w-ppm, calculated as elemental sulfur, preferably from 0 to 1000 w-ppm and most preferably from 0 to 500 w-ppm. In one embodiment sulfur is deliberately introduced into the reaction zone together with the feedstock in order to control the catalytic reactions and hydrotreatment catalyst stability. Sulfur may further originate from the feedstock.

The liquid feed flow rate WHSV is preferably from 0.1 to 10 l/h, more preferably from 0.1 to 5 l/h, most preferably from 0.1 to 3 l/h. Minimising the flow increases the conversion.

The deoxygenation of plant oils/fats and animal fats with hydrogen (HDO) requires rather much hydrogen and at the same time releases significant amount of heat. Heat is formed from deoxygenation reactions and double bond hydrogenation. Different feedstock produce significantly different amount of reaction heat. The variations of reaction heat formed is mainly dependent of double bond hydrogenation, therefore, the feed sources like palm oil or animal fat, which have more saturated fatty acid derivatives, produce less heat. The average amount of double bonds per triglyceride molecule can vary from about 1.5 to over 5 depending on the source of bio oil or fat (iodine number from 50 to over 150).

One preferable way to handle reaction heat in this invention is to use reaction conditions, which only partly deoxygenate triglycerides or fatty acids or fatty acid derivatives. This again favours ketonisation of fatty acids, because too efficient deoxygenation destroys the carboxylic acid groups in fatty acids and therefore the starting material for the ketonization reaction. The partial hydrogenation or deoxygenation can be done using a hydrogen addition, which is lower than the theoretical chemical consumption of hydrogen needed for complete deoxygenation.

Advantageously according to the present invention co-production of base oil components and fuel components is possible to perform simultaneously using these low hydrogen amounts and low product recycle dilution with stable operation. The amounts of the produced components or ratio thereof may be regulated by adjustment of reaction conditions such as temperature, pressure and hydrogen amount.

The ketonisation reaction under hydrogen pressure provides ketones and paraffins which may be further treated by deoxygenation and/or isomerization in single or multiple steps.

Final Hydrodeoxygenation Step

The reaction product from combined ketonisation/hydrotreatment step is preferably hydrodeoxygenated in a further final hydrodeoxygenation (HDO) step. This is preferably carried out under a hydrogen gas partial pressure ranging from 0.1 to 20 MPa, more preferably from 1 and 15 MPa, most preferably from 2 to 10 MPa. The temperature ranges preferably from 100 to 500 C, more preferably from 150 to 400 C, most preferably from 200 to 350 C. The flow rate, WHSV, is preferably varied from 0.1 to 10 l/h, more preferably from WHSV 1 to 5 l/h, and most preferably from WHSV 1 to 3 l/h. In this final HDO step, catalysts containing a hydrogenation metal, on a support are used. Preferably, the HDO catalyst is a supported Pd, Pt, Ni, NiMo or CoMo catalyst, the support being activated carbon, alumina and/or silica.

The product obtained after the final HDO step is preferably purified for instance by stripping with steam, or with a suitable gas such as a light hydrocarbons, nitrogen or hydrogen. It is advantageous to remove impurities (i.e. H2S, NH3, H2O, CO2, CO) as efficiently as possible prior to isomerization step and/or finishing steps.

Isomerization Step

Isomerization of diesel (C10-C23) and base oil (C24-C43) components from final hydrodeoxygenation step is preferably done together to give isoparaffins. Isomerisation is done in order to improve cold flow properties. Hydroisomerization of diesel paraffins is known and is typically performed using noble metal bifunctional catalysts, preferably Pt-SAPO or Pt-ZSM-catalysts, at a reaction temperature of 300-400° C., pressure of 2-5 MPa and WHSV from 0.5 to 2 $h^{-1}$ with hydrogen. Isomerization of n-paraffins does not as such need hydrogen, but it is important that olefins formed from cracking (side reaction) are quickly hydrogenated. Without the fast olefin saturation, coking of catalyst is observed.

Due to the longer chains of base oil range n-paraffins (C24-C43) compared to diesel paraffins (carbon number typically below 24), isomerization is more challenging. In order to get good cold flow properties of the longer chained n-paraffins more severe isomerization is needed. At the same time the probability of cracking is higher when n-paraffins are longer. However, when C24-C43 hydrocarbons crack, excellent diesel and jet hydrocarbons are produced. This is one advantage of this combined production scheme.

In addition, the processing may include several other steps such as distillations steps before or after the isomerisation step.

In the second aspect of the present invention a method for simultaneous production of base oil components and fuel components is provided, comprising the steps of
  (i) introducing a feedstock comprising fatty acids and/or fatty acid esters into a reaction zone, and
  (ii) subjecting said feedstock to a ketonisation reaction in said reaction zone in the presence of a dual catalyst system configured to perform a ketonisation reaction and a hydrotreatment reaction under hydrogen pressure, and
  (iii) subjecting ketones resulting from step (ii) to a hydrodeoxygenation step to form linear hydrocarbons, and
  (iv) introducing said linear hydrocarbons resulting from step (ii) and (iii) into an isomerization unit under isomerization conditions wherein a mixture of branched hydrocarbons is formed, and
  (v) separating from said mixture of branched hydrocarbons components suitable for use as base oil, having a carbon number range from C24-C43, from hydrocarbons suitable for use as fuel components, having a carbon number range from C5 to C23.

In a preferred process sequence, the treatment of renewable feedstock comprises combined ketonisation/hydrotreatment, final hydrodeoxygenation, isomerisation and final separation of the fuel components and the base oil components.

The present invention provides an integrated production process having less unit operations and reaction steps. There is no need of selective double bond hydrogenation unit or free fatty acid separation from triglycerides (distillation unit) and low grade animal fats having high amount of free fatty acids (10-40% by weight FFA) can be used. Moreover, there is no need for prior vaporisation of fatty acids due to lack of high flow carrier gas circulation resulting in smaller operation units. The hydrotreating catalyst is resistant to sulfur and nitrogen compounds.

The process of the present invention provides after isomerisation very high quality base oil components together with very high quality diesel fuel components. Moreover, cracking during isomerization yields excellent diesel components and biojet components. High quality diesel component has high cetane index over 60 and comprises isoparaffins, does not contain olefins, and has low aromatic content, or does not contain any aromatics. Present invention also provides a biojet component, which has excellent cold flow properties (freezing point below −42° C.), is stable and has high volumetric energy content.

In the third aspect of the present invention a dual catalyst system is provided.

During the combined ketonisation and hydrotreatment step, such as hydrodeoxygenation step, a dual catalyst system is applied. This catalyst system is configured to perform a ketonisation reaction and a hydrotreatment reaction.

The ketonisation reaction is preferably provided by metal oxide catalyst (ketonisation catalyst) component. The metals of these metal oxides are selected from the group consisting of Na, Mg, K, Ca, Sc, Cr, Mn, Fe, Co, Ni, Cu, Zn, Sr, Ti, Y, Zr, Mo, Rh, Cd, Sn, La, Pb, Bi, Ti, V and other rare earth metals and combination thereof. The metal is more preferably selected from the group of potassium, titanium, manganese, magnesium, iron and/or calcium or combination thereof, most preferably the metal is potassium or titanium or combination thereof. No special catalysts are needed for the ketonisation of specific components such as metal salts of fatty acids (+2 valence metal soaps like calcium, barium iron, magnesium etc), since the metal present in the soap promotes the ketonisation reaction (pyrogenic decomposition of metal carboxylates).

The hydrotreatment reaction is preferably provided by a metal catalyst (hydrotreatment catalyst) component selected from the group consisting of Fe, Pd, Pt, Ni, Mo, Co, Ru, Rh, W and any combination thereof. More preferably, the metals are Ni, Co, Mo, W or any combination thereof, optionally with additional Mn, Fe, Pd, Pt metals. Most preferably, the catalyst is NiMo.

Preferably, the metal oxide catalyst and the metal catalyst are supported i.e. on a support. Preferred supports are laterite, bauxite, titanium dioxide, active carbon, silica and/or aluminium oxide, most preferably active carbon, silica and alumina.

In a preferred embodiment the dual catalyst system comprises a mixture or combination of a ketonisation catalyst configured to perform said ketonisation reaction and a hydrotreatment catalyst configured to perform said hydrotreatment reaction.

In one embodiment these two catalyst types are combined in a single catalyst material.

In one embodiment, the mixed catalyst is made by mixing a hydrotreatment catalyst material with a ketonisation catalyst material.

In another preferred embodiment the ketonisation metal oxide, preferably $K_2O/TiO_2$, and the hydrotreatment metal, preferably NiMo, catalysts are bound to a common support, preferably alumina.

Preferably, the dual catalyst system comprises a sulfided hydrotreatment and/or ketonisation catalyst. This system may be combined or mixed ketonisation and hydrotreatment catalyst which is sulfided. Sulfidation is provided by conventional treatments.

In a yet preferred embodiment the dual catalyst system comprises $K_2O/TiO_2$ providing the ketonisation reaction activity and NiMo providing the hydrotreatment reaction activity. More preferably, these active materials are on a support, preferably on an alumina, silica or active carbon support. Most preferably, the active hydrotreatment catalyst is further sulfided.

Preferably, the dual catalyst system contains 40-90% by weight of the ketonisation catalyst, more preferably 70-90% by weight of ketonisation catalyst.

In a fourth aspect of the present invention a production system for simultaneous production of base oil components and fuel components is provided. This system comprises:

16. A production system for simultaneous production of base oil components and fuel components, comprising:

(a) at least one reaction unit comprising at least one reaction zone including a dual catalyst system configured to perform a ketonisation reaction and a hydrotreatment reaction under hydrogen pressure for producing ketones and linear hydrocarbons; and (b) at least one reaction unit comprising at least one reaction zone configured to perform hydrodeoxygenation to said ketones into linear hydrocarbons; and (c) at least one reaction unit comprising at least one reaction zone configured to isomerize said linear hydrocarbons; and (d) at least one distillation installation configured to separate base oil components from fuel components;

wherein at least one reaction unit (a) is connected to at least one reaction unit (b), and wherein at least one reaction unit (b) is connected to at least one distillation installation (c), and wherein at least one reaction unit (c) is connected to at least one distillation installation (d), wherein the system further comprises a flow path for recycling hydrocarbons from unit (b), (c) or (d) back to unit (a).

In one embodiment of the production system the units (a) and/or (b) and/or (c) comprise at least two reactions zones in series.

In order to control the increase of temperature over catalyst beds, fresh bio-oil feed can be divided between several catalyst beds. Hydrotreated product can be recycled back to the reactor feed.

The present invention is further illustrated by the following non-limiting examples.

EXAMPLES

Example 1

A mixture of stearic acid and palm oil was subjected to combined ketonisation and hydrotreatment in the presence of sulfidised $K_2O/TiO_2$—NiMo dual catalyst system. The catalyst system was prepared by crushing an alumina supported NiMo catalyst and a $K_2O/TiO_2$ catalyst and thoroughly mixing the two together. The reaction was carried out using hydrogen to hydrocarbon ($H_2$/HC) ratio of 500 Nl/l and a weight hourly space velocity (WHSV) of $1.0\ h^{-1}$. Three separate tests (test I, test II and test III) were conducted and the other process conditions and hydrocarbon distribution of the product form is shown in table 1.

TABLE 1

Process conditions and product distribution of the various tests

| Test | T °C. | P Mpa | C11-C23 %* | ≥C24 %* |
|---|---|---|---|---|
| I | 340 | 2 | 80.9 | 2.1 |
| II | 365 | 2 | 79.1 | 4.1 |
| III | 365 | 0.6 | 74 | 7.6 |

*The rest of the product formed is light hydrocarbon gas and water

The product obtained in test III was distilled in reduced pressure to two separate fraction and the base oil fraction (>C24) was analysed. The kinematic viscosities of the base oil fraction in various temperatures are shown in table 2.

TABLE 2

Viscosities of product from test III

| | Temperature [° C.] | | |
|---|---|---|---|
| | 40 | 80 | 100 |
| Viscosity [mm2/s] | 23.3 | 8.08 | 5.5 |

The viscosity index (VI) was 186. The viscosities were measured according to EN ISO 3104 standard and the viscosity index was calculated according to ASTM 2270 standard.

Example 2

A mixture of stearic acid (30 wt-%) and palm oil (70 wt-%) was subjected to a combined ketonisation and hydrotreatment process. The process was carried out in the presence of a sulphidized $K_2O/TiO_2$—NiMo dual catalyst system prepared as in Example 1. The ratio of $K_2O/TiO_2$ to NiMo on alumina support was 50:50 wt-%. The process conditions were as follows Temperature of 365° C.,
Pressure of 0.6 MPa, H
Hydrogen to hydrocarbon ($H_2$/HC) ratio of 500 Nl/l and
Weight hourly space velocity (WHSV) of 1.0 1/h.

TABLE 3

Product distribution

| Gas + $H_2O$ $C_{1-4}$ | Gasoline $C_{5-10}$ | Diesel $C_{11-23}$ | Base oil $\geq C_{24}$ |
|---|---|---|---|
| 17.8 | 0.3 | 73.0 | 8.7 |

The product obtained was analyzed with gas chromatography. The obtained GC chromatogram confirms the formation of linear C33 and C35 paraffins. The GC chromatogram also shows some peaks which were identified as ketones.

The product obtained was also distillated in reduced pressure to two separate fractions and analyzed. Properties of produced base oil components and properties fuel fraction components are presented in Table 4 and 5.

TABLE 4

Base oil component (lube component) from the process, prior to isomerisation

| ENISO3104 | Viscosity 40° C. | mm2/s | 23.35 |
| ENISO3104 | Viscosity 80° C. | mm2/s | 8.08 |
| ENISO3104 | Viscosity 100° C. | mm2/s | 5.499 |
| ASTMD2270 | VI | | 186 |
| ASTMD7346 M | Pour point | ° C. | >45 |

TABLE 5

Fuel component (diesel, kerosene, naphta) from the process, prior to isomerisation

| ENISO12185 | Density | kg/m3 | 790.5 |
| NM473 | Cloud point | ° C. | 22.5 |
| ENISO3104 | Viscosity 40° C. | mm2/s | 3.106 |
| ENISO4264 | cetane index | | >56.5 |
| ENISO3405 | IBP | ° C. | 246.4 |
| ENISO3405 | 5 | ° C. | 278.1 |
| ENISO3405 | 10 | ° C. | 279.2 |
| ENISO3405 | 15 | ° C. | 281 |
| ENISO3405 | 20 | ° C. | 282.1 |

TABLE 5-continued

Fuel component (diesel, kerosene, naphta) from the process, prior to isomerisation

| ENISO3405 | 30 | ° C. | 283.9 |
| ENISO3405 | 40 | ° C. | 285.6 |
| ENISO3405 | 50 | ° C. | 287.6 |
| ENISO3405 | 60 | ° C. | 289.6 |
| ENISO3405 | 70 | ° C. | 282 |
| ENISO3405 | 80 | ° C. | 295.1 |
| ENISO3405 | 85 | ° C. | 297.1 |
| ENISO3405 | 90 | ° C. | 300 |
| ENISO3405 | 95 | ° C. | 303.6 |
| ENISO3405 | FBP | ° C. | 321.4 |
| ASTMD7346 M | Pour point | ° C. | 1 |
| ASTMD7039 | Sulphur | mg/kg | 18.6 |
| ASTMD976 | Cetane Index | | 73.3 |

Example 3

The reaction of example 2 was repeated with a mixture of palm oil fatty acid (30 wt-%) and palm oil (70 wt-%), except for using a pressure of 2 MPa (instead of 0.6 MPa in example 2). Similar product distribution was achieved with the use of palm oil fatty acid (PFAD) instead of pure stearic acid, with only a slight decrease in the base oil yield (5.5%>C24 compared to 7.6% in example 2).

The product obtained was distilled in reduced pressure to two separate fractions and analyzed. Properties of produced base oil components and properties fuel fraction components are presented in Table 6 and 7.

TABLE 6

Base oil component (lube component) from the process, prior to isomerisation

| ENISO3104 | Viscosity 40° C. | mm2/s | 23.09 |
| ENISO3104 | Viscosity 80° C. | mm2/s | 7.928 |
| ENISO3104 | Viscosity 100° C. | mm2/s | 5.385 |
| ASTMD2270 | VI | | 181 |
| ASTMD7346 M | Pour point | ° C. | >45 |

TABLE 7

Fuel component (diesel, kerosene, naphta) from the process, prior to isomerisation

| ENISO12185 | Density | kg/m3 | 784.7 |
| NM473 | Cloud point | ° C. | 20.6 |
| ENISO3104 | Viscosity 40° C. | mm2/s | 3.185 |
| ENISO4264 | Cetane Index | | >>56.5 |
| ENISO3405 | IBP | ° C. | 262.8 |
| ENISO3405 | 5 | ° C. | 276.3 |
| ENISO3405 | 10 | ° C. | 278.1 |
| ENISO3405 | 15 | ° C. | 279.7 |
| ENISO3405 | 20 | ° C. | 280.6 |
| ENISO3405 | 30 | ° C. | 282.4 |
| ENISO3405 | 40 | ° C. | 284.1 |
| ENISO3405 | 50 | ° C. | 285.9 |
| ENISO3405 | 60 | ° C. | 288 |
| ENISO3405 | 70 | ° C. | 290.6 |
| ENISO3405 | 80 | ° C. | 294 |
| ENISO3405 | 85 | ° C. | 296.3 |
| ENISO3405 | 90 | ° C. | 299.3 |
| ENISO3405 | 95 | ° C. | 306.4 |
| ENISO3405 | FBP | ° C. | 320 |
| ASTMD7346 M | Pour point | ° C. | 15 |
| ASTMD7039 | Sulphur | mg/kg | 11.4 |
| ASTMD976 | Cetane Index | | 75.4 |

The results show that excellent base oil components are achieved from a mixture of fatty acids (palm oil fatty acids)

and mainly triglyceridic material (palm oil). The base oil components are achieved without sacrificing the quality of the fuel components.

Example 4

Palm oil (100%) was subjected to combined ketonisation and hydrotreatment process. The process was carried out in presence of a sulphidized $K_2O/TiO_2$—NiMo dual catalyst system prepared as in Example 1. The ratio of $K_2O/TiO_2$ to NiMo on alumina support was 50:50 wt-%. The process conditions were as follows:
temperature of 365° C.,
pressure of 4 MPa,
hydrogen to hydrocarbon ($H_2$/HC) ratio of 500 Nl/l and weight hourly space velocity (WHSV) of 1.0 1/h.
Hydrocarbon distribution yields, and water yields are presented in table 8.

TABLE 8

Product distribution

| Gas + $H_2O$ $C_{1-4}$ | Gasoline $C_{5-10}$ | Diesel $C_{11-23}$ | Base oil $\geq C_{24}$ |
|---|---|---|---|
| 15.2 | 0.3 | 80.2 | 4.3 |

The product obtained was distilled at reduced pressure into two separate fractions and analysed. Properties of the produced base oil components and fuel fraction components are presented in Tables 9 and 10.

TABLE 9

Base oil component (lube component) from the process, prior to isomerisation

| ENISO3104 | Viscosity 40° C. | mm2/s | 27.69 |
|---|---|---|---|
| ENISO3104 | Viscosity 80° C. | mm2/s | 9.058 |
| ENISO3104 | Viscosity 100° C. | mm2/s | 6.054 |
| ASTMD2270 | VI | | 175 |
| ASTMD7346 M | Pour point | ° C. | >45° C. |

TABLE 10

Fuel component (diesel, kerosene, naphta) from the process, prior to isomerisation

| ENISO12185 | Density | kg/m3 | 784.6 |
|---|---|---|---|
| NM473 | Cloud point | ° C. | 19.6 |
| ENISO3104 | Viscosity 40° C. | mm2/s | 3.324 |
| ENISO4264 | Cetane Index | | >>56.5 |
| ENISO3405 | IBP | ° C. | 266.4 |
| ENISO3405 | 5 | ° C. | 280 |
| ENISO3405 | 10 | ° C. | 281.5 |
| ENISO3405 | 15 | ° C. | 282.9 |
| ENISO3405 | 20 | ° C. | 283.8 |
| ENISO3405 | 30 | ° C. | 285.4 |
| ENISO3405 | 40 | ° C. | 287 |
| ENISO3405 | 50 | ° C. | 288.8 |
| ENISO3405 | 60 | ° C. | 290.7 |
| ENISO3405 | 70 | ° C. | 293.2 |
| ENISO3405 | 80 | ° C. | 296.4 |
| ENISO3405 | 85 | ° C. | 298.6 |
| ENISO3405 | 90 | ° C. | 301.7 |
| ENISO3405 | 95 | ° C. | na |
| ENISO3405 | FBP | ° C. | 320.9 |
| ASTMD7346 M | Pour point | ° C. | 18 |
| ASTMD7039 | Sulphur | mg/kg | <2 |
| ASTMD976 | Cetane Index | | 76 |

The results show that excellent base oil components are achieved from a triglyceridic raw material (palm oil). Palm oil does not readily contain free fatty acids. The results indicate that the triglyceridic material decompose to components (fatty acids) that can undergo ketonization reaction and produce hydrocarbons with longer chain lengths, compared to the chain lengths of the feedstock fatty acids.

Example 5

A mixture of palm oil fatty acid (30 wt-%) and palm oil (70 wt-%) was subjected to combined ketonisation and hydrotreatment (CKH). The CKH was carried out in presence of sulphidized $K_2O/TiO2$-NiMo prepared as in Example 1 but with a $K_2O/TiO_2$ to NiMo ratio of 80:20 wt-%. Conditions were: temperature of 365° C. and under a pressure of 2 MPa, using hydrogen to hydrocarbon ($H_2$/HC) ratio of 500 Nl/l and weight hourly space velocity (WHSV) of 1.0 1/h.

Liquid product obtained from CHK was passed through a final hydrodeoxygenation step, in presence of a sulphidized NiMo catalyst at temperature of 295° C. and under a pressure of 5 MPa, using hydrogen to hydrocarbon ($H_2$/HC) ratio of 1000 Nl/l and weight hourly space velocity (WHSV) of 1.0 1/h. Hydrocarbon distribution yields, and water yields are presented in table 11.

TABLE 11

Product distribution after CKH and final hydrodeoxygenation step

| Gas + H2O C1-4 | Gasoline C5-10 | Diesel C11-23 | Base oil $\geq C24$ |
|---|---|---|---|
| 0.3 | 0.8 | 68.5 | 30.5 |

Hydrogenated n-paraffin product obtained was distilled in reduced pressure to two separate fractions and analyzed. Properties of produced base oil component and properties of fuel fraction component are presented in Table 12 and 13.

TABLE 12

Base oil component (lube component) prior isomerisation

| ENISO3104 | Viscosity 40° C. | mm2/s | 22.98 |
|---|---|---|---|
| ENISO3104 | Viscosity 80° C. | mm2/s | 8.008 |
| ENISO3104 | Viscosity 100° C. | mm2/s | 5.462 |
| ASTMD2270 | VI | | 188 |
| ASTMD7346 M | Pour point | ° C. | >45 |

TABLE 13

Fuel component (diesel, kerosene, naphtha) prior isomerisation

| ENISO12185 | Density | kg/m3 | 785.5 |
|---|---|---|---|
| NM473 | Cloud point | ° C. | 24.2 |
| ENISO3104 | Viscosity 40° C. | mm2/s | 3.284 |
| ENISO4264 | Setane index | | >>56.5 |
| ENISO3405 | IBP | ° C. | 258.6 |
| ENISO3405 | 5 | ° C. | 273.6 |
| ENISO3405 | 10 | ° C. | 276.8 |
| ENISO3405 | 15 | ° C. | 278.5 |
| ENISO3405 | 20 | ° C. | 279.8 |
| ENISO3405 | 30 | ° C. | 282.1 |
| ENISO3405 | 40 | ° C. | 284 |
| ENISO3405 | 50 | ° C. | 286.2 |
| ENISO3405 | 60 | ° C. | 288.7 |
| ENISO3405 | 70 | ° C. | 291.8 |
| ENISO3405 | 80 | ° C. | 296.4 |

TABLE 13-continued

Fuel component (diesel, kerosene, naphtha) prior isomerisation

| | | | |
|---|---|---|---|
| ENISO3405 | 85 | ° C. | 299.7 |
| ENISO3405 | 90 | ° C. | 306.1 |
| ENISO3405 | FBP | ° C. | 333 |
| ASTMD7346 M | Pour point | ° C. | 18 |
| ASTMD7039 | Sulphur | mg/kg | 1.83 |
| ASTMD976 | Setane Index | | 75.1 |

Liquid hydrocarbons from final HDO were subjected to isomerisation. Isomerisation was carried out in presence of noble metal bi-functional catalyst at temperature of 311° C. and under a pressure of 5 MPa, using hydrogen to hydrocarbon ($H_2$/HC) ratio of 800 Nl/l and weight hourly space velocity (WHSV) of 1.0 1/h. Process conditions, hydrocarbon distribution yields are presented in table 14.

TABLE 14

Process conditions in Isomerisation and product distribution

| Catalyst | Reactor T, P | $H_2$/HC, WHSV |
|---|---|---|
| Isom | 311° C., 5 MPa | 800, 1.0 |

| Gas $C_{1-4}$ | Gasoline $C_{5-10}$ | Diesel $C_{11-23}$ | Base oil $\geq C_{24}$ |
|---|---|---|---|
| 1 | 5 | 69 | 25 |

Isomerized liquid product obtained from isomerisation was distillated in reduced pressure to 3 separate fractions and analyzed. Properties of fractionated base oil and properties of fractionated kerosene and diesel are presented in Table 15, 16 and 17.

TABLE 15

Base oil component (lube component) Isomerized product. Cut point 380° C.

| | | | |
|---|---|---|---|
| ENISO12185 | Density | kg/m3 | 824.7 |
| ASTMD5771 | Cloud point | ° C. | −10 |
| ASTMD5950 | Pour point | ° C. | −15 |
| ENISO3104 | Viskosity 40° C. | mm2/s | 24.48 |
| ENISO3104 | Viskosity 100° C. | mm2/s | 5.284 |
| ASTMD5293 | CCS-35° C. | mPas | 2830 |
| ASTMD5293 | CCS-30° C. | mPas | 1580 |
| ASTMD2270 | VI | | 156 |

TABLE 16

Fuel component (diesel) Isomerized product. Cut point 270-380° C.

| | | | |
|---|---|---|---|
| ENISO12185 | Density | kg/m3 | 788.7 |
| ASTMD5771 | Cloud point | ° C. | −32 |
| ASTMD5950 | Pour point | ° C. | −51 |
| EN116 | CFPP | ° C. | −32 |
| ENISO3104 | Viskosity 40° C. | mm2/s | 3.613 |
| ENISO2719 | Flash point | ° C. | 139 |
| ASTMD6890 | Setane | | 79.4 |
| ENISO3405 | IBP | ° C. | 275.3 |
| ENISO3405 | 5 | ° C. | 284.7 |
| ENISO3405 | 10 | ° C. | 285.9 |
| ENISO3405 | 20 | ° C. | 286.9 |
| ENISO3405 | 30 | ° C. | 287.7 |
| ENISO3405 | 40 | ° C. | 288.8 |
| ENISO3405 | 50 | ° C. | 289.9 |
| ENISO3405 | 60 | ° C. | 291.4 |
| ENISO3405 | 70 | ° C. | 293.1 |

TABLE 16-continued

Fuel component (diesel) Isomerized product. Cut point 270-380° C.

| | | | |
|---|---|---|---|
| ENISO3405 | 80 | ° C. | 295.9 |
| ENISO3405 | 90 | ° C. | 301.3 |
| ENISO3405 | 95 | ° C. | 308.4 |
| ENISO3405 | FBP | ° C. | 319.1 |

TABLE 17

Fuel component (kerosene) Isomerized product. Cut point 270° C.

| | | | |
|---|---|---|---|
| ENISO12185 | Density | kg/m3 | 774.3 |
| ASTMD5771 | Cloud point | ° C. | −46 |
| ASTMD5950 | Pour point | ° C. | <−70 |
| IP529 | Freezing point | ° C. | −42.5 |
| NM438 | Conductivity | µS/cm | 0.35 |
| ENISO3405 | IBP | ° C. | 210.5 |
| ENISO3405 | 5 | ° C. | 233.6 |
| ENISO3405 | 10 | ° C. | 239 |
| ENISO3405 | 20 | ° C. | 247.3 |
| ENISO3405 | 30 | ° C. | 253.1 |
| ENISO3405 | 40 | ° C. | 256.9 |
| ENISO3405 | 50 | ° C. | 259.6 |
| ENISO3405 | 60 | ° C. | 261.7 |
| ENISO3405 | 70 | ° C. | 263.7 |
| ENISO3405 | 80 | ° C. | 266 |
| ENISO3405 | 90 | ° C. | 269.4 |
| ENISO3405 | 95 | ° C. | 272.8 |
| ENISO3405 | FBP | ° C. | 276.8 |

The invention claimed is:

1. A method for simultaneous production of components suitable for production of base oil and fuel components, comprising the steps of:
   a) introducing a feedstock comprising fatty acids and/or fatty acid esters into a reaction zone, and
   b) subjecting said feedstock to a ketonisation reaction in said reaction zone in the presence of a dual catalyst system configured to perform a ketonisation reaction and a hydrotreatment reaction, under hydrogen pressure, and
   c) obtaining from said ketonisation reaction ketones in addition to linear hydro-carbons from said fatty acids and/or fatty acid esters.

2. The method according to claim 1, wherein said obtained ketones are further hydrodeoxygenated to form linear hydrocarbons.

3. The method according to claim 1, wherein said fatty acid esters are triglycerides.

4. The method according to claim 1, wherein said feedstock is at least partly in liquid form when entered into said reaction zone.

5. The method according to claim 1, wherein the pressure in said reaction zone is less than 10 MPa.

6. The method according to claim 1, wherein the temperature in said reaction zone is from 200 to 450° C.

7. The method according to claim 1, wherein the ratio of hydrogen to feedstock is from 100 to 600 Nl/l.

8. A method for simultaneous production of base oil components and fuel components, comprising the steps of
   (i) introducing a feedstock comprising fatty acids and/or fatty acid esters into a reaction zone, and
   (ii) subjecting said feedstock to a ketonisation reaction in said reaction zone in the presence of a dual catalyst system configured to perform a ketonisation reaction and a hydrotreatment reaction under hydrogen pressure, and (iii) subjecting ketones resulting from step (ii) to a hydrodeoxygenation step to form linear hydrocarbons, and (iv) introducing said linear hydrocarbons resulting from step (ii) and (iii) into an isomenzation unit under isomenzation conditions wherein a mixture of branched hydrocarbons is formed, and (v) separating from said mixture of branched hydrocarbons components suitable for use as base oil, having a carbon number range from C24-C43, from hydrocarbons suitable for use as fuel components, having a carbon number range from C5 to C23.

9. A production system for simultaneous production of base oil components and fuel components, comprising:

(a) at least one reaction unit comprising at least one reaction zone including a dual catalyst system configured to perform a ketonisation reaction and hydrotreatment reaction under hydrogen pressure for producing ketones and linear hydrocarbons; and (b) at least one reaction unit comprising a least one reaction zone configured to perform hydrodeoxygenation to said ketones into linear hydrocarbons; and (c) at least one reaction unit comprising at least one reaction zone configured to isomerize said linear hydrocarbons; and (d) at least one distillation installation configured to separate base oil components from fuel components;

wherein at least one reaction unit (a) is connected to at least one reaction unit (b), and wherein at least one reaction unit (b) is connected to at least one distillation installation (c), and wherein at least one reaction unit (c) is connected to at least one distillation installation (d), wherein the system further comprises a flow path for recycling hydrocarbons from unit (b), (c) or (d) back to unit (a).

10. The method according to claim 1, wherein said feedstock is completely in liquid form when entered into said reaction zone.

11. The method according to claim 1, wherein the pressure in said reaction zone is from 0.1 to 5 MPa.

12. The method according to claim 1, wherein the ratio of hydrogen to feedstock is from 100 to 500 Nl/l.

* * * * *